US00PP28097P2

(12) United States Plant Patent
Lee

(10) Patent No.: US PP28,097 P2
(45) Date of Patent: Jun. 13, 2017

(54) ***RHODODENDRON* PLANT NAMED 'BAILEA'**

(50) Latin Name: ***Rhododendron* hybrid**
Varietal Denomination: BAILEA

(71) Applicant: Robert Edward Lee, Independence, LA (US)

(72) Inventor: Robert Edward Lee, Independence, LA (US)

( * ) Notice: Subject to any disclaimer, the term of this patent is extended or adjusted under 35 U.S.C. 154(b) by 0 days.

(21) Appl. No.: 14/998,400

(22) Filed: Dec. 31, 2015

(51) Int. Cl.
*A01H 5/00* (2006.01)

(52) U.S. Cl.
USPC ..... Plt./240

(58) Field of Classification Search
USPC ..... Plt./240
See application file for complete search history.

*Primary Examiner* — Annette Para
(74) *Attorney, Agent, or Firm* — Cassandra Bright

(57) ABSTRACT

A new and distinct *Rhododendron* cultivar named 'BAILEA' is disclosed, characterized by distinctive semi-double red and red-purple flowers. Plants bloom Spring, Summer and Fall and exhibit good tolerance to environmental stressors. Plants are very well suited for performance in the landscape, including as a specimen plant or a hedge. The new cultivar is a *Rhododendron*, suitable for ornamental garden purposes.

2 Drawing Sheets

Figure 1:
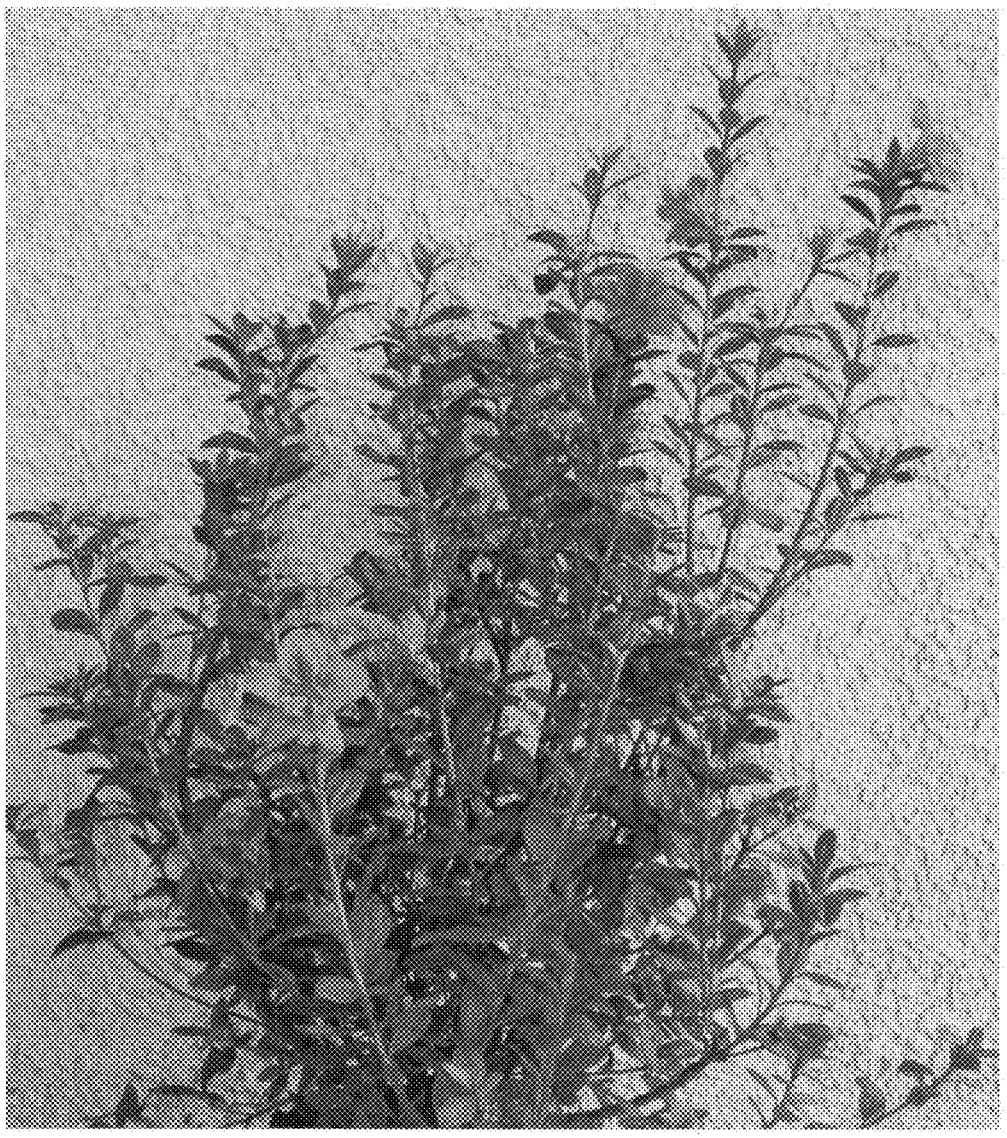

Latin name of the genus and species: *Rhododendron* hybrid.

Variety denomination: 'BAILEA'.

BACKGROUND OF THE INVENTION

The new cultivar is a product of a planned breeding program by the inventor, Robert Edward Lee. The inventor's intention was to develop *Rhododendron* hybrid plants with re-blooming characteristics and good landscape performance. This new variety, hereinafter referred to as 'BAILEA', was discovered as a seedling, resulting from the crossing of *Rhododendron* 'May Blaine, unpatented with the pollen parent *Rhododendron* 'Fourth of July', unpatented. The cross resulting in the new variety occurred during the Spring of 1994. The new variety was selected by the inventor during November of 1996 at a commercial nursery in Independence, La.

After identifying the new variety as a potentially interesting selection, the inventor first organized propagation of 'BAILEA' by vegetative cuttings Fall of 1998 at the same commercial nursery in Independence, La. The inventor continued controlled testing and propagation, assessing stability of the unique characteristics of this variety. At least three generations have been reproduced and have shown that the unique features of this cultivar are stable and reproduced true to type.

SUMMARY OF THE INVENTION

The cultivar 'BAILEA' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BAILEA' These characteristics in combination distinguish 'BAILEA' as a new and distinct *Rhododendron* cultivar:

1. Unique Spring, Summer, and Fall blooming.
2. Semi-double flowers.
3. Self-Cleaning flowers
4. Tolerant of a variety of environmental stressors.
5. Plants very well suited for landscape use, including hedge planting or as a specimen.
7. Observed hardy to Zone 7 and potentially Zone 6.

COMPARISON TO PARENT VARIETY

'BAILEA' is similar in most horticultural characteristics to the seed parent *Rhododendron* hybrid 'May Blaine'. Plants of the new cultivar 'BAILEA' however differ in the following:

1. The new variety has a red-purple flower, the seed parent has a light lavender flower.
2. The new variety blooms more consistently over three seasons, the seed parent blooms in Spring.
3. Plants of the new variety are more compact than the seed parent.
4. Flowers of the new variety are semi-double, flowers of the parent variety are most commonly double, with some semi-double flowers on the plant.
5. Plants of the new variety are better suited for landscape use.

'BAILEA' is similar in most horticultural characteristics to the pollen parent *Rhododendron* hybrid 'Fourth of July'. Plants of the new cultivar 'BAILEA' however differ in the following:

1. Plants of the new variety are more compact than plants of the pollen parent.
2. Plants of the new variety are better suited for landscape use.
3. Plants of the new variety have stronger, less sensitive roots than plants of the pollen parent.
4. Plants of the new variety are more tolerant of environmental stressors than plants of the pollen parent.

5. Plants of the new variety are more Winter hardy than plants of the pollen parent.

COMMERCIAL COMPARISON

'BAILEA' can be compared to the commercial variety *Rhododendron* hybrid 'Roblec' U.S. Plant Pat. No. 15,339. Plants of the new cultivar 'BAILEA' are similar to plants of 'Roblec' in most horticultural characteristics, however, plants of the new cultivar 'BAILEA' differ in the following:

1. 'Bailea' has flowers colored near Red 54B and Red-Purple 64D; flowers of 'Roblec' are colored near Red-Purple 73B.
2. Plants of 'Bailea' grow more vigorously than plants of 'Roblec'.
3. Foliage of 'Bailea' is sub-opposite and obovate, foliage of 'Roblec' is alternate and elliptic.

'BAILEA' can be compared to the commercial variety *Rhododendron* hybrid 'Conlea' U.S. Plant Pat. No. 10,438. Plants of the new cultivar 'BAILEA' are similar to plants of 'Conlea' in most horticultural characteristics, however, plants of the new cultivar 'BAILEA' differ in the following;

1. 'Bailea' has flowers colored Red and Red-Purple, near Red 54B and Red-Purple 64D, 'Conlea' has flowers which are solid Red, colored near Red 54A
2. Foliage of 'Bailea' is sub-opposite and obovate, foliage of 'Conlea' is alternate and elliptic.

BRIEF DESCRIPTION OF THE PHOTOGRAPHS

The accompanying photograph in FIG. 1 illustrates in full color a 2 year old plant of the new variety in a 3 gallon pot.

Figure 2:
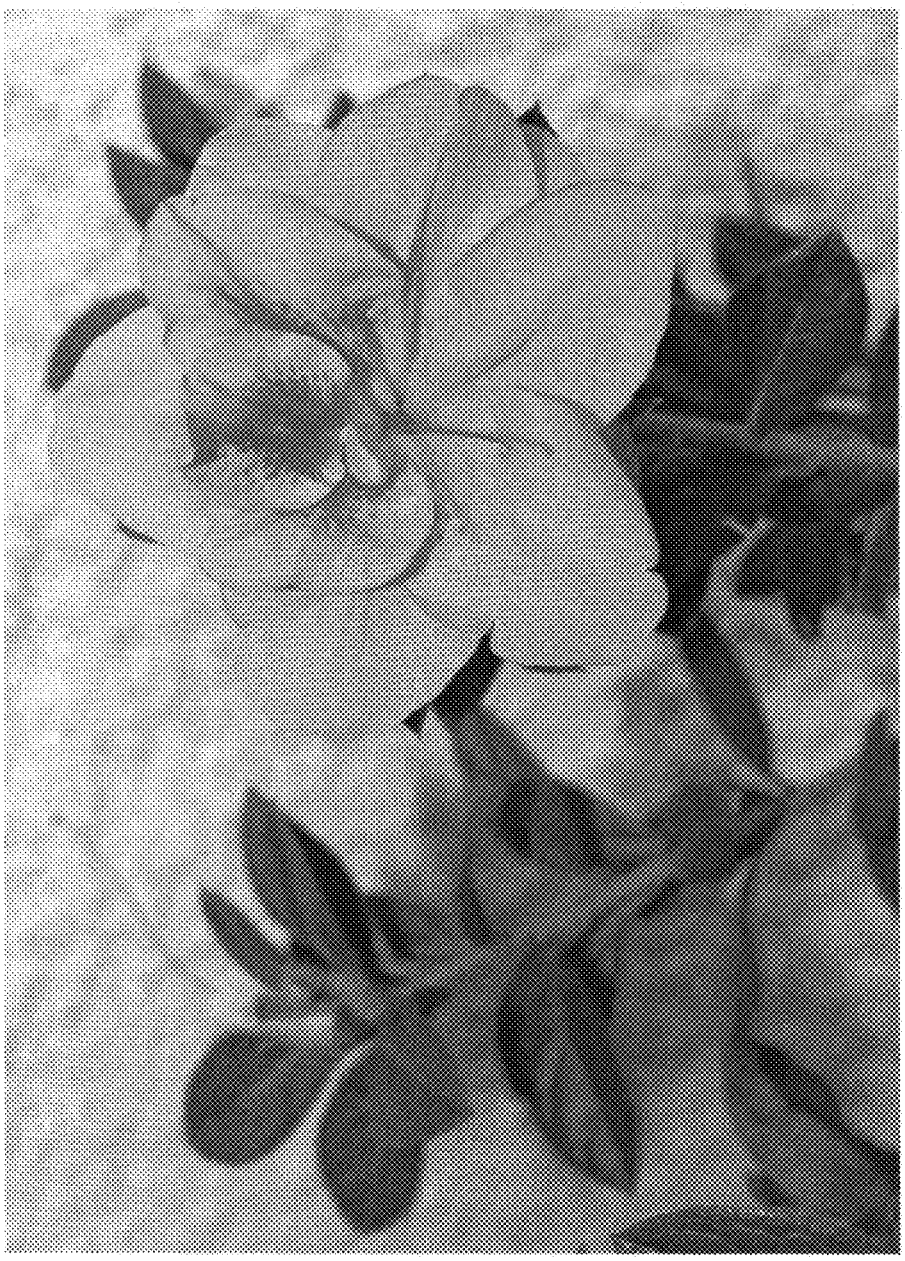

FIG. 2 illustrates in full color a close up of typical flowers of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BAILEA' plants grown outdoors in Loxley, Ala. Plants are approximately 2 years old, in a 3 gallon nursery container. Measurements and numerical values represent averages of typical plant types.

Botanical classification: *Rhododendron* hybrid 'BAILEA'.

PROPAGATION

Typically by semi-hardwood cuttings in Spring and Summer.

Root description: Fine, fibrous young roots, well branched. Colored near RHS Grey-Brown 199A.

PLANT

Growth habit: Upright evergreen shrub.

Height: Approximately 75 cm to top of foliar and flowering plane.

Plant spread: Approximately 68 cm.

Branching characteristics: Well branched, approximately 3 to 6 primary branches from the center of the plant. Branches occur at approximately 15° to 30° angles. Each primary branch has 4 to 8 lateral branches.

Primary branches:

*Length of primary branches*.—Average range 25 to 40 cm.

*Diameter of primary branches*.—Approximately 1.0 cm.

*Primary branch strength*.—Very strong, difficult to break.

*Primary branch color*.—Near Greyed-Orange 177A, streaked 177B.

*Primary branch texture*.—Scaly, rough.

Lateral branches:

*Number of lateral branches*.—Approximately 4 to 8 per primary branch.

*Length of lateral branches*.—Average range 20 to 30 cm.

*Diameter of lateral branches*.—Average 0.3 to 0.6 cm.

*Lateral branch strength*.—Very strong, flexible.

*Lateral branch color*.—New growth near RHS Greyed-Red 181A, next stage, near RHS Yellow-Green 152D; oldest branches become woody, colored near Greyed-Orange 177A.

*Lateral branch texture*.—Immature growth hirsute. Older growth scaly, hirsute. Hairs semi-appressed and colored near Greyed-Orange 175C.

*Internode length*.—Average 3.0 cm.

*Age of plant described*.—Approximately 2 years.

FOLIAGE

Leaf:

*Type*.—Simple.

*Arrangement*.—Sub-opposite.

*Average length*.—Approximately 4.7 cm.

*Average width*.—Approximately 2.2 cm.

*Shape of blade*.—Obovate.

*Apex*.—Acute to nearly mucronate.

*Base*.—Broad attenuate.

*Attachment*.—Stalked.

*Margin*.—Entire. Cilliate.

*Texture of top surface*.—Pubescent. Hairs appressed, very short, rough.

*Texture of bottom surface*.—Pubescent. Longer hairs present along main vein and margin.

*Color*.—Young foliage upper side: Near RHS Yellow-Green 144A, slightly darker. Young foliage under side: Near RHS Green 138B. Mature foliage upper side: Near RHS Green 137A. Mature foliage under side: Near RHS Yellow-Green 147B.

*Venation*.—Type: Pinnate. Venation color upper side: Near RHS Yellow-Green 144C. Venation color under side: Near RHS Yellow-Green 151A.

*Petiole*.—Length: About 0.5 cm. Diameter: About 0.15 cm. Color: Upper Surface: Near RHS Yellow-Green 146D. Lower Surface: Near RHS Yellow-Green 151B.

FLOWER

Bloom period: Plants begin flowering in the Spring, and continue to produce flowers throughout Summer and Fall.

Flower:

*Arrangement*.—Axillary clusters of perfect, open funnel shaped individual flowers. Typically 3 to 5 flowers per cluster.

Inflorescence:
*Height*.—Average 10.0 cm.
*Diameter*.—Average 12.0 cm.
Peduncle: Not present, inflorescence pedicels emerge directly from node.
Pedicel:
*Length*.—Average 0.5 cm to 1.5 cm.
*Diameter*.—0.3 cm.
*Color*.—Near RHS Red 53C.
*Texture*.—Densely pubescent. Long, soft hairs colored near White N155B.
*Aspect*.—Straight. Angle of attachment, approximately 45° angle from stem.
*Strength*.—Very sturdy and flexible.
Flowers:
*Length*.—Average 4.2 cm.
*Diameter*.—Average 6.5 cm.
*Facing direction*.—Outwardly and upwardly facing.
*Persistent or self-cleaning*.—Self-cleaning.
*Fragrance*.—Very faint.
Tube:
*Tube length*.—Approximately 2.2 cm.
*Tube width a widest point*.—Approximately 1.5 cm.
*Tube width and narrowest point*.—Approximately 0.9 cm.
Petals:
*Unfused petal segments*.—Length: Approximately 2.9 cm. Width: Approximately 2.7 cm.
*Apex*.—Blunt, rounded. Occasionally retuse.
*Shape of petal*.—Unfused portion, obovate.
*Petal margin*.—Entire. Aspect very slightly undulating.
*Petal arrangement*.—Overlapping, bilateral symmetry dissecting bottom petal. Petals fused approximately ½ distance from base.
*Petal number*.—5 full petals. 3 to 5 irregularly shaped and sized petaloids in center of flower.
*Petal texture*.—Smooth.
Color:
*Upper surface at first opening*.—Near RHS Red-Purple 63A near margins, 63B in center. Dotted near Red-Purple 59B.
*Under surface at first opening*.—Near RHS Red-Purple 63B.
*Inner surface at maturity*.—Near RHS Red 54B, 3 upper petals dotted with Red-Purple 61A.
*Outer surface at maturity*.—Near RHS Red-Purple 64D.
*Upper surface at fading*.—Near RHS Red 54B, 3 upper petals more heavily dotted with Red-Purple 61A.
*Under surface at fading*.—Near RHS Red-Purple 62A.
Bud:
*Shape*.—Elliptic.
*Length*.—5.0 cm.
*Diameter*.—1.8 cm.
*Color*.—Near RHS Red-Purple N57D.
Calyx/sepals:
*Quantity per flower*.—5 sepals.
*Shape*.—Narrow deltate.
*Length*.—0.7 cm.
*Width*.—0.4 cm.
*Apex*.—Acute.
*Base*.—Fused.
*Margin*.—Entire.
*Texture*.—Highly pubescent, sericeous. Color: Inner Surface: Near RHS Yellow-Green 145A, lower margin and base flushed near Red-Purple 59B. Outer Surface: Near RHS Yellow-Green 145A, lower margin and base flushed near Red-Purple 59D.

REPRODUCTIVE ORGANS

Stamens:
*Number*.—5, fused to petaloids at irregular lengths. Some stamens fully fused, with only anther unfused, some stamens 10% fused to petaloids.
*Stamen length*.—1.8 to 2.6 cm.
*Width*.—0.1 cm.
*Color*.—Near RHS Red-Purple N57A.
*Anthers*.—Length: Approximately 0.3 cm. Color: Near RHS Greyed-Yellow 61D. Pollen: Not observed.
Pistil:
*Number*.—1.
*Length*.—Average range 3.9 cm to 6.0 cm.
*Style*.—Length: Average 3.5 cm to 5.6 cm. Color: Near RHS Red 53B.
*Stigma*.—Globular, colored near Red 53B.
*Ovary*.—Sericeous texture. Approximately 0.4 cm in diameter. Colored near Yellow-Green 145A.

OTHER CHARACTERISTICS

Disease and pest resistance: Not observed to be susceptible nor resistant to normal diseases and pests of *Rhododendron*.
Temperature tolerance: Observed hardy to USDA Zone 7, potentially hardy to zone 6.
Fruit/seed production: Not observed to date.

What is claimed is:

1. A new and distinct cultivar of *Rhododendron* plant named 'BAILEA' as herein illustrated and described.

* * * * *